(12) United States Patent
Chroboczek et al.

(10) Patent No.: US 6,750,058 B1
(45) Date of Patent: Jun. 15, 2004

(54) TRANSFECTING PEPTIDE VECTOR, COMPOSITION CONTAINING SAME AND APPLICATIONS

(75) Inventors: Jadwiga Chroboczek, Grenoble (FR); Pascal Fender, Grenoble (FR)

(73) Assignees: Commissariat a l'Energie Atomique, Paris (FR); Centre National de la Recherche Scientifique-CNRS, Paris (FR)

( * ) Notice: Subject to any disclaimer, the term of this patent is extended or adjusted under 35 U.S.C. 154(b) by 0 days.

(21) Appl. No.: 09/530,560

(22) PCT Filed: Nov. 3, 1998

(86) PCT No.: PCT/FR98/02344

§ 371 (c)(1),
(2), (4) Date: May 19, 2000

(87) PCT Pub. No.: WO99/23237

PCT Pub. Date: May 14, 1999

(30) Foreign Application Priority Data

Nov. 3, 1997 (FR) .............................................. 97 13771

(51) Int. Cl.[7] .......................... C12N 15/87; C07K 4/02; C07K 14/075
(52) U.S. Cl. ................. 435/455; 435/235.1; 435/320.1; 435/456; 530/324; 530/325; 530/326; 530/327; 530/328; 530/329; 530/330; 536/23.1
(58) Field of Search ................................. 435/455, 456, 435/235.1, 320.1; 536/23.1; 530/324, 325, 326, 327, 328, 329, 330; 514/2, 44

(56) References Cited

U.S. PATENT DOCUMENTS 6,083,720 A * 7/2000 Chroboczek et al. ...... 435/69.1

FOREIGN PATENT DOCUMENTS

| WO | WO 94/17832 | 8/1994 |
| WO | WO 97/18317 | 5/1997 |
| WO | WO 97/20575 | 6/1997 |

OTHER PUBLICATIONS

Signas et al., J. Virol., 1985, vol. 53, No. 2, pp. 672–678.*
Kajon et al., Virology, 1996, vol. 215, pp. 190–1996.*
Fender, P. et al.; "Adenovirus dodecahedron, a new vector for human gene transfer," *Nature Biotechnology*, vol. 15, Jan. 1997, pp. 52–56, XP002071995; Grenoble, France.
Hong, J.S. et al.; "The Amino Terminus of the Adenovirus Fiber Protein Encodes the Nuclear Localization Signal," *Virology*, vol. 18, No. 2, Dec. 1991, pp. 758–767, XP000607409.
Clever, J. et al.: "Simian virus 40 Vp2/3 small structural proteins harbor their own nuclear transport signal," *Virology*, vol. 181, No. 1, Mar. 1991, pp. 78–90. XP002097033.

* cited by examiner

*Primary Examiner*—David Guzo
(74) *Attorney, Agent, or Firm*—Alston & Bird LLP

(57) ABSTRACT

The invention concerns transfecting peptide vector, a composition containing said vector and their applications for treating and preventing diseases in human beings and animals. Said vector for transfecting a chemical substance selected in the group consisting of nucleic acid sequences, proteins, peptides and pharmacologically active substances, contains besides said chemical substance, at least a transfecting peptide derived entirely or partially from an adenovirus fibre and comprising at least a zone consisting of at least 50% hydrophobic amino acids selected in the group consisting of alanine, valine, phenylamine, isoleucine, leucine, proline and methionine.

14 Claims, 7 Drawing Sheets

```
AD11p  1  MT·KRVRLS···················DSFNPVYPYEDESTSQ··HPFINPGF  (SEQ ID NO:26)
AD11a  1  MT·KRVRLS···················DSFNPVYPYEDESTSQ··HPFINPGF  (SEQ ID NO:27)
AD7    1  MT·KRVRLS···················DSFNPVYPYEDESTSQ··HPFINPGF  (SEQ ID NO:28)
AD21   1  MT·KRVRLS···················DSFNPVYPYEDESTSQ··HPFINPGF  (SEQ ID NO:29)
AD3    1  MA·KRARLS···················TSFNPVYPYEDESSSQ··HPFINPGF  (SEQ ID NO:30)
AD16   1  MA·KRARLS···················SSFNPVYPYEDESSSQ··HPFINPGF  (SEQ ID NO:31)
AD2    1  M··KRARPS···················EDTFNPVYPYDTETGPPT··VPFLTPPF (SEQ ID NO:32)
AD5    1  M··KRARPS···················EDTFNPVYPYDTETGPPT··VPFLTPPF (SEQ ID NO:33)
AD4    1  MSKKRARV····················DDGFDPVYPYDADNA·PT··VPFINPPF (SEQ ID NO:34)
AD12   1  M··KRSRTQYAEETEENDDFNPVYPFDPFDTSD··VPFVTPPF              (SEQ ID NO:35)
AD8    1  MT·KRLRA····················EDDFNPVYPYGYARNQN··IPFLTPPF  (SEQ ID NO:36)
AD9    1  MS·KRLRV····················EDDFNPVYPYGYARNQN··IPFLTPPF  (SEQ ID NO:37)
AD15   1  MS·KRLRV····················EDDFNPVYPYGYARNQN··IPFLTPPF  (SEQ ID NO:38)
AD41-1 1  M··KRARL····················EDDFNPVYPYEHYN·PLD··IPFITPPF (SEQ ID NO:39)
AD40-1 1  M··KRARF····················EDDFNPVYPYEHYN·PLD··IPFITPPF (SEQ ID NO:40)
AD40-2 1  M··KRTRI····················EDDFNPVYPYDTSS·TPS··IPYVAPPF (SEQ ID NO:41)
AD41-2 1  M··KRTRI····················EDDFNPVYPYDTFS·TPS··IPYVAPPF (SEQ ID NO:42)
```

FIG. 7.

SEQUENCE LISTING

<160> NUMBER OF SEQ ID NOS: 49

<210> SEQ ID NO 1
<211> LENGTH: 5
<212> TYPE: PRT
<213> ORGANISM: Adenoviridae
<220> FEATURE:
<221> NAME/KEY: VARIANT
<222> LOCATION: 1
<223> OTHER INFORMATION: Xaa = Any Amino Acid

<400> SEQUENCE: 1

Xaa Lys Arg Val Arg
 1               5

<210> SEQ ID NO 2
<211> LENGTH: 5
<212> TYPE: PRT
<213> ORGANISM: Adenoviridae
<220> FEATURE:
<221> NAME/KEY: VARIANT
<222> LOCATION: 1
<223> OTHER INFORMATION: Xaa = Any Amino Acid

<400> SEQUENCE: 2

Xaa Lys Arg Ala Arg
 1               5

<210> SEQ ID NO 3
<211> LENGTH: 5
<212> TYPE: PRT
<213> ORGANISM: Adenoviridae
<220> FEATURE:
<221> NAME/KEY: VARIANT
<222> LOCATION: 1
<223> OTHER INFORMATION: Xaa = Any Amino Acid

<400> SEQUENCE: 3

Xaa Lys Arg Ser Arg
 1               5

```
<210> SEQ ID NO 4
<211> LENGTH: 5
<212> TYPE: PRT
<213> ORGANISM: Adenoviridae
<220> FEATURE:
<221> NAME/KEY: VARIANT
<222> LOCATION: 1
<223> OTHER INFORMATION: Xaa = Any Amino Acid

<400> SEQUENCE: 4

Xaa Lys Arg Leu Arg
 1               5

<210> SEQ ID NO 5
<211> LENGTH: 5
<212> TYPE: PRT
<213> ORGANISM: Adenoviridae
<220> FEATURE:
<221> NAME/KEY: VARIANT
<222> LOCATION: 1
<223> OTHER INFORMATION: Xaa = Any Amino Acid

<400> SEQUENCE: 5

Xaa Lys Arg Thr Arg
 1               5

<210> SEQ ID NO 6
<211> LENGTH: 6
<212> TYPE: PRT
<213> ORGANISM: Adenoviridae
<220> FEATURE:
<221> NAME/KEY: VARIANT
<222> LOCATION: 1
<223> OTHER INFORMATION: Xaa = Any Amino Acid

<400> SEQUENCE: 6

Xaa Pro Lys Lys Pro Arg
 1               5

<210> SEQ ID NO 7
<211> LENGTH: 9
<212> TYPE: PRT
<213> ORGANISM: Adenoviridae
<220> FEATURE:
<221> NAME/KEY: VARIANT
<222> LOCATION: 1, 9
<223> OTHER INFORMATION: Xaa = Any Amino Acid

<400> SEQUENCE: 7

Xaa Phe Asn Pro Val Tyr Pro Tyr Xaa
 1               5

<210> SEQ ID NO 8
<211> LENGTH: 9
<212> TYPE: PRT
<213> ORGANISM: Adenoviridae
<220> FEATURE:
<221> NAME/KEY: VARIANT
<222> LOCATION: 1, 9
<223> OTHER INFORMATION: Xaa = Any Amino Acid

<400> SEQUENCE: 8

Xaa Phe Asp Pro Val Tyr Pro Tyr Xaa
 1               5

<210> SEQ ID NO 9
<211> LENGTH: 4
<212> TYPE: PRT
```

```
<213> ORGANISM: Adenoviridae

<400> SEQUENCE: 9

Leu Ser Asp Ser
 1

<210> SEQ ID NO 10
<211> LENGTH: 4
<212> TYPE: PRT
<213> ORGANISM: Adenoviridae

<400> SEQUENCE: 10

Leu Ser Thr Ser
 1

<210> SEQ ID NO 11
<211> LENGTH: 4
<212> TYPE: PRT
<213> ORGANISM: Adenoviridae

<400> SEQUENCE: 11

Leu Ser Ser Ser
 1

<210> SEQ ID NO 12
<211> LENGTH: 5
<212> TYPE: PRT
<213> ORGANISM: Adenoviridae

<400> SEQUENCE: 12

Pro Ser Glu Asp Thr
 1               5

<210> SEQ ID NO 13
<211> LENGTH: 4
<212> TYPE: PRT
<213> ORGANISM: Adenoviridae

<400> SEQUENCE: 13

Val Asp Asp Gly
 1

<210> SEQ ID NO 14
<211> LENGTH: 12
<212> TYPE: PRT
<213> ORGANISM: Adenoviridae

<400> SEQUENCE: 14

Thr Gln Tyr Ala Glu Glu Thr Glu Glu Asn Asp Asp
 1               5                  10

<210> SEQ ID NO 15
<211> LENGTH: 4
<212> TYPE: PRT
<213> ORGANISM: Adenoviridae
<220> FEATURE:
<221> NAME/KEY: VARIANT
<222> LOCATION: 1
<223> OTHER INFORMATION: Xaa = Any Amino Acid

<400> SEQUENCE: 15

Xaa Glu Asp Asp
 1

<210> SEQ ID NO 16
```

```
<211> LENGTH: 4
<212> TYPE: PRT
<213> ORGANISM: Adenoviridae

<400> SEQUENCE: 16

Glu Asp Glu Ser
 1

<210> SEQ ID NO 17
<211> LENGTH: 4
<212> TYPE: PRT
<213> ORGANISM: Adenoviridae

<400> SEQUENCE: 17

Asp Thr Glu Thr
 1

<210> SEQ ID NO 18
<211> LENGTH: 4
<212> TYPE: PRT
<213> ORGANISM: Adenoviridae

<400> SEQUENCE: 18

Asp Ala Asp Asn
 1

<210> SEQ ID NO 19
<211> LENGTH: 4
<212> TYPE: PRT
<213> ORGANISM: Adenoviridae

<400> SEQUENCE: 19

Asp Pro Phe Asp
 1

<210> SEQ ID NO 20
<211> LENGTH: 4
<212> TYPE: PRT
<213> ORGANISM: Adenoviridae

<400> SEQUENCE: 20

Gly Tyr Ala Arg
 1

<210> SEQ ID NO 21
<211> LENGTH: 4
<212> TYPE: PRT
<213> ORGANISM: Adenoviridae

<400> SEQUENCE: 21

Glu His Tyr Asn
 1

<210> SEQ ID NO 22
<211> LENGTH: 4
<212> TYPE: PRT
<213> ORGANISM: Adenoviridae

<400> SEQUENCE: 22

Asp Thr Ser Ser
 1

<210> SEQ ID NO 23
<211> LENGTH: 4
<212> TYPE: PRT
```

<213> ORGANISM: Adenoviridae

<400> SEQUENCE: 23

Asp Thr Phe Ser
 1

<210> SEQ ID NO 24
<211> LENGTH: 9
<212> TYPE: PRT
<213> ORGANISM: Adenoviridae

<400> SEQUENCE: 24

Gly Pro Asn Lys Lys Lys Arg Lys Leu
 1               5

<210> SEQ ID NO 25
<211> LENGTH: 7
<212> TYPE: PRT
<213> ORGANISM: Rhesus macaque polyomavirus

<400> SEQUENCE: 25

Pro Lys Lys Lys Arg Lys Val
 1               5

<210> SEQ ID NO 26
<211> LENGTH: 32
<212> TYPE: PRT
<213> ORGANISM: Adenoviridae

<400> SEQUENCE: 26

Met Thr Lys Arg Val Arg Leu Ser Asp Ser Phe Asn Pro Val Tyr Pro
 1               5                  10                  15

Tyr Glu Asp Glu Ser Thr Ser Gln His Pro Phe Ile Asn Pro Gly Phe
                20                  25                  30

<210> SEQ ID NO 27
<211> LENGTH: 32
<212> TYPE: PRT
<213> ORGANISM: Adenoviridae

<400> SEQUENCE: 27

Met Thr Lys Arg Val Arg Leu Ser Asp Ser Phe Asn Pro Val Tyr Pro
 1               5                  10                  15

Tyr Glu Asp Glu Ser Thr Ser Gln His Pro Phe Ile Asn Pro Gly Phe
                20                  25                  30

<210> SEQ ID NO 28
<211> LENGTH: 32
<212> TYPE: PRT
<213> ORGANISM: Adenoviridae

<400> SEQUENCE: 28

Met Thr Lys Arg Val Arg Leu Ser Asp Ser Phe Asn Pro Val Tyr Pro
 1               5                  10                  15

Tyr Glu Asp Glu Ser Thr Ser Gln His Pro Phe Ile Asn Pro Gly Phe
                20                  25                  30

<210> SEQ ID NO 29
<211> LENGTH: 32
<212> TYPE: PRT
<213> ORGANISM: Adenoviridae

<400> SEQUENCE: 29

```
Met Thr Lys Arg Val Arg Leu Ser Asp Ser Phe Asn Pro Val Tyr Pro
  1               5                  10                  15

Tyr Glu Asp Glu Ser Thr Ser Gln His Pro Phe Ile Asn Pro Gly Phe
                 20                  25                  30

<210> SEQ ID NO 30
<211> LENGTH: 32
<212> TYPE: PRT
<213> ORGANISM: Adenoviridae

<400> SEQUENCE: 30

Met Ala Lys Arg Ala Arg Leu Ser Thr Ser Phe Asn Pro Val Tyr Pro
  1               5                  10                  15

Tyr Glu Asp Glu Ser Ser Ser Gln His Pro Phe Ile Asn Pro Gly Phe
                 20                  25                  30

<210> SEQ ID NO 31
<211> LENGTH: 32
<212> TYPE: PRT
<213> ORGANISM: Adenoviridae

<400> SEQUENCE: 31

Met Ala Lys Arg Ala Arg Leu Ser Ser Ser Phe Asn Pro Val Tyr Pro
  1               5                  10                  15

Tyr Glu Asp Glu Ser Ser Ser Gln His Pro Phe Ile Asn Pro Gly Phe
                 20                  25                  30

<210> SEQ ID NO 32
<211> LENGTH: 33
<212> TYPE: PRT
<213> ORGANISM: Adenoviridae

<400> SEQUENCE: 32

Met Lys Arg Ala Arg Pro Ser Glu Asp Thr Phe Asn Pro Val Tyr Pro
  1               5                  10                  15

Tyr Asp Thr Glu Thr Gly Pro Pro Thr Val Pro Phe Leu Thr Pro Pro
                 20                  25                  30

Phe

<210> SEQ ID NO 33
<211> LENGTH: 33
<212> TYPE: PRT
<213> ORGANISM: Adenoviridae

<400> SEQUENCE: 33

Met Lys Arg Ala Arg Pro Ser Glu Asp Thr Phe Asn Pro Val Tyr Pro
  1               5                  10                  15

Tyr Asp Thr Glu Thr Gly Pro Pro Thr Val Pro Phe Leu Thr Pro Pro
                 20                  25                  30

Phe

<210> SEQ ID NO 34
<211> LENGTH: 33
<212> TYPE: PRT
<213> ORGANISM: Adenoviridae

<400> SEQUENCE: 34

Met Ser Lys Lys Arg Ala Arg Val Asp Gly Phe Asp Pro Val Tyr
  1               5                  10                  15

Pro Tyr Asp Ala Asp Asn Ala Pro Thr Val Pro Phe Ile Asn Pro Pro
                 20                  25                  30
```

Phe

<210> SEQ ID NO 35
<211> LENGTH: 39
<212> TYPE: PRT
<213> ORGANISM: Adenoviridae

<400> SEQUENCE: 35

Met Lys Arg Ser Arg Thr Gln Tyr Ala Glu Glu Thr Glu Glu Asn Asp
1               5                   10                  15

Asp Phe Asn Pro Val Tyr Pro Phe Asp Pro Phe Asp Thr Ser Asp Val
            20                  25                  30

Pro Phe Val Thr Pro Pro Phe
        35

<210> SEQ ID NO 36
<211> LENGTH: 32
<212> TYPE: PRT
<213> ORGANISM: Adenoviridae

<400> SEQUENCE: 36

Met Thr Lys Arg Leu Arg Ala Glu Asp Asp Phe Asn Pro Val Tyr Pro
1               5                   10                  15

Tyr Gly Tyr Ala Arg Asn Gln Asn Ile Pro Phe Leu Thr Pro Pro Phe
            20                  25                  30

<210> SEQ ID NO 37
<211> LENGTH: 32
<212> TYPE: PRT
<213> ORGANISM: Adenoviridae

<400> SEQUENCE: 37

Met Ser Lys Arg Leu Arg Val Glu Asp Asp Phe Asn Pro Val Tyr Pro
1               5                   10                  15

Tyr Gly Tyr Ala Arg Asn Gln Asn Ile Pro Phe Leu Thr Pro Pro Phe
            20                  25                  30

<210> SEQ ID NO 38
<211> LENGTH: 32
<212> TYPE: PRT
<213> ORGANISM: Adenoviridae

<400> SEQUENCE: 38

Met Ser Lys Arg Leu Arg Val Glu Asp Asp Phe Asn Pro Val Tyr Pro
1               5                   10                  15

Tyr Gly Tyr Ala Arg Asn Gln Asn Ile Pro Phe Leu Thr Pro Pro Phe
            20                  25                  30

<210> SEQ ID NO 39
<211> LENGTH: 31
<212> TYPE: PRT
<213> ORGANISM: Adenoviridae

<400> SEQUENCE: 39

Met Lys Arg Ala Arg Leu Glu Asp Asp Phe Asn Pro Val Tyr Pro Tyr
1               5                   10                  15

Glu His Tyr Asn Pro Leu Asp Ile Pro Phe Ile Thr Pro Pro Phe
            20                  25                  30

<210> SEQ ID NO 40
<211> LENGTH: 31

```
<212> TYPE: PRT
<213> ORGANISM: Adenoviridae

<400> SEQUENCE: 40

Met Lys Arg Ala Arg Phe Glu Asp Asp Phe Asn Pro Val Tyr Pro Tyr
 1               5                  10                  15

Glu His Tyr Asn Pro Leu Asp Ile Pro Phe Ile Thr Pro Pro Phe
            20                  25                  30

<210> SEQ ID NO 41
<211> LENGTH: 31
<212> TYPE: PRT
<213> ORGANISM: Adenoviridae

<400> SEQUENCE: 41

Met Lys Arg Thr Arg Ile Glu Asp Asp Phe Asn Pro Val Tyr Pro Tyr
 1               5                  10                  15

Asp Thr Ser Ser Thr Pro Ser Ile Pro Tyr Val Ala Pro Pro Phe
            20                  25                  30

<210> SEQ ID NO 42
<211> LENGTH: 31
<212> TYPE: PRT
<213> ORGANISM: Adenoviridae

<400> SEQUENCE: 42

Met Lys Arg Thr Arg Ile Glu Asp Asp Phe Asn Pro Val Tyr Pro Tyr
 1               5                  10                  15

Asp Thr Phe Ser Thr Pro Ser Ile Pro Tyr Val Ala Pro Pro Phe
            20                  25                  30

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence:PEPTIDE

<400> SEQUENCE: 43

Lys Ile Pro Ile Lys
 1               5

<210> SEQ ID NO 44
<211> LENGTH: 40
<212> TYPE: PRT
<213> ORGANISM: Artificial Sequence
<220> FEATURE:
<223> OTHER INFORMATION: Description of Artificial Sequence:PEPTIDE

<400> SEQUENCE: 44

Ala Lys Arg Ala Arg Leu Ser Thr Ser Phe Asn Pro Val Tyr Pro Tyr
 1               5                  10                  15

Glu Asp Glu Ser Lys Lys Lys Lys Lys Lys Lys Lys Lys Lys
            20                  25                  30

Lys Lys Lys Lys Lys Lys Lys Lys
            35                  40

<210> SEQ ID NO 45
<211> LENGTH: 30
<212> TYPE: PRT
<213> ORGANISM: Artificial Sequence
<220> FEATURE:
<223> OTHER INFORMATION: Description of Artificial Sequence:PEPTIDE
```

<400> SEQUENCE: 45

Ala Lys Arg Ala Arg Leu Ser Thr Ser Phe Asn Pro Val Tyr Pro Tyr
 1               5                  10                  15
Glu Asp Glu Ser Lys Lys Lys Lys Lys Lys Lys Lys
            20                  25                  30

<210> SEQ ID NO 46
<211> LENGTH: 23
<212> TYPE: PRT
<213> ORGANISM: Artificial Sequence
<220> FEATURE:
<223> OTHER INFORMATION: Description of Artificial Sequence:PEPTIDE

<400> SEQUENCE: 46

Ala Lys Arg Ala Arg Leu Ser Thr Ser Glu Asp Glu Ser Lys Lys Lys
 1               5                  10                  15
Lys Lys Lys Lys Lys Lys Lys
            20

<210> SEQ ID NO 47
<211> LENGTH: 35
<212> TYPE: PRT
<213> ORGANISM: Artificial Sequence
<220> FEATURE:
<223> OTHER INFORMATION: Description of Artificial Sequence:PEPTIDE

<400> SEQUENCE: 47

Leu Ser Thr Ser Phe Asn Pro Val Tyr Pro Tyr Glu Asp Glu Ser Lys
 1               5                  10                  15
Lys Lys Lys Lys Lys Lys Lys Lys Lys Lys Lys Lys Lys Lys Lys
            20                  25                  30
Lys Lys Lys
        35

<210> SEQ ID NO 48
<211> LENGTH: 20
<212> TYPE: PRT
<213> ORGANISM: Artificial Sequence
<220> FEATURE:
<223> OTHER INFORMATION: Description of Artificial Sequence:PEPTIDE

<400> SEQUENCE: 48

Ala Lys Arg Ala Arg Leu Ser Thr Ser Phe Asn Pro Val Tyr Pro Tyr
 1               5                  10                  15
Glu Asp Glu Ser
            20

<210> SEQ ID NO 49
<211> LENGTH: 41
<212> TYPE: PRT
<213> ORGANISM: Artificial Sequence
<220> FEATURE:
<223> OTHER INFORMATION: Description of Artificial Sequence:PEPTIDE
<220> FEATURE:
<221> NAME/KEY: THIOETH
<222> LOCATION: (20)..(21)
<220> FEATURE:
<221> NAME/KEY: THIOETH
<222> LOCATION: (21)..(22)
<220> FEATURE:
<221> NAME/KEY: PEPTIDE
<222> LOCATION: (21)
<223> OTHER INFORMATION: POLYLYSINE(K18) PEPTIDE BRANCHD TO LYSINE AT
      POSITION 21

<400> SEQUENCE: 49

-continued

```
Ala Lys Arg Ala Arg Leu Ser Thr Ser Phe Asn Pro Val Tyr Pro Tyr
 1               5                  10                  15

Glu Asp Glu Ser Lys Ser Glu Asp Tyr Pro Tyr Val Pro Asn Phe
                20                  25              30

Ser Thr Ser Leu Arg Ala Arg Lys Ala
        35              40
```

TRANSFECTING PEPTIDE VECTOR, COMPOSITION CONTAINING SAME AND APPLICATIONS

BACKGROUND OF THE INVENTION

The present invention relates to a transfecting peptide vector, to a composition containing the said vector as well as to their applications in the treatment (medicaments) and the prevention (vaccines) of human and animal diseases. The said vector is in particular capable of dispensing to suitable target cells nucleic sequences, proteins, peptides and chemical substances of interest.

In the field of gene therapy, many compositions useful for efficiently transfecting eukaryotic cells with a selected genetic material have been described.

There are essentially two main types of transfection vectors:
  the natural transfection vectors, such as viruses or modified viruses, which are efficient but which have limits to their use: tissue nonspecificity, necessity to obtain constructs for each gene of interest and potential risks for the environment which lead to the setting in place of costly and constraining clinical infrastructures for the patient and staff;
  nonviral agents (synthetic vectors), capable of promoting the transfer and the expression of chemical substances such as DNA into eukaryotic cells. The latter strategy represents an alternative to viral vectors.

These synthetic vectors must essentially have two functions: to condense the DNA to be transfected and to promote its cellular attachment as well as its passage across the plasma membrane and possibly the nuclear membranes; such vectors must therefore mimic the functioning of viruses in order to be efficient; however, it appears that the different vectors provided in the prior art do not exhibit these two functions in an optimum manner and may, in addition, depending on the cases, be toxic for the cells.

Among these nonviral agents, there may be mentioned first of all the cationic polymers and the cationic lipids. The former generally consist of polylysine, whereas a wide variety of cationic lipids (liposomes or pseudoliposomes) exist, each giving transfection efficiencies which vary according to the cell types (DOTMA, and the like).

The lipid portion which interacts with and/or destabilizes the membranes allows the fusion and the entry of the DNA/liposome complex.

However, the transfection of DNA by liposomes, although less immunogenic than that performed with the aid of cationic polymers, is in fact a relatively inefficient method.

The major mechanism of entry of the DNA/liposome complexes is, it seems, endocytosis; consequently, the transfected DNA is trapped in the intracellular vesicles and destroyed by the lysosomal enzymes.

Even if a portion of the transfected DNA is released into the cytoplasm by a mass action effect, only a small fraction of this DNA is effectively present in the nucleus.

Agents capable of increasing the release of the DNA from the endosomal vesicles and its passage into the nucleus can increase the gene transfer rate.

Among these agents, there may be distinguished:
  those which target the complex towards another point of entry: the targeting is obtained, for example, by coupling ligands with the polylysine polymers; the targeting can also occur after internalization, by directing the complexes to the nucleus (PCT International Application WO 95/31557), and
  those which avoid endosomal degradation; to escape endosomal degradation, it has been proposed to incorporate an endosomolytic agent into the complex, such as adenoviral particles (PCT International Application WO 93/07283) or more recently synthetic peptides with endosomolytic activity, which increase the release of the DNA into the cytoplasm.

Taking into account the preceding text, various types of complexes have been provided; there may be mentioned complexes combining liposomes and peptides, such as those described in:
  International Application WO 96/25508, which describes compositions comprising (i) the nucleic acid to be transfected, (ii) a transfection agent, such as a cationic polymer and/or a lipofectant, (iii) a peptide compound involved at the level of the condensation of the nucleic acid, consisting as a whole or in part of peptide motifs possessing a majority of amino acids with a basic character, such as lysine, histidine, arginine (histones, nucleolin, protamine or derivatives thereof) and optionally (iv) a targeting element which makes it possible to orient the transfer of the nucleic acid, such as a ligand of the intracellular type such as a nuclear localization signal sequence (NLS) which favours the accumulation of the transfected DNA inside the nucleus and which may be combined with the peptide compound to form a chimeric peptide comprising a protein fragment (histone or protamine or nucleolin) and an NLS sequence. However, this system requires the presence of a cationic polymer and/or a lipofectant, which have the disadvantage of being toxic and/or costly,
  International Application WO 97/30170 which also describes compositions for transfecting eukaryotic cells, which comprise the nucleic acid to be transfected, at least one cationic lipid at a suboptimal concentration and at least one acidic peptide (active on the membrane) which destabilizes the endosomal membrane and thus increases the transfection efficiency. The positive charge/negative charge ratio is between 0 and 3. The selected peptides are derived from the influenza virus, so as to induce effective rupture of the endosomes. The presence of the lipids is necessary in this composition because of the fact that the selected peptide does not allow passage across the first cell membrane.

Such complexes do not therefore make it possible to avoid the disadvantages linked to the use of liposomes.

That is undoubtedly the reason why complexes using only peptides have been provided:
  European Patent Application 0,544,292, which describes a complex for transfecting nucleic acid which comprises a fusion protein consisting of a cellular factor (growth factor, viral antigen, toxin, integrin or lipoprotein) and a basic polycationic peptide comprising arginine and/or lysine residues,
  International Application WO 94/23751, which describes a transfer peptide which comprises three parts: (1) a ligand L1 (peptide of 2 to 100 amino acids), capable of binding to a binding site at the surface of eukaryotic cells (membrane receptor) (example: peptide RGD, domain for binding of growth factors, hormones, viral antigens or lipoproteins), (2) a ligand L2 similar to L1 (peptide of 2 to 20 amino acids), which binds to the outer nuclear membrane of eukaryotic cells, such as an NLS sequence and (3) a ligand L3 corresponding to a basic peptide (3 to 100 amino acids) (histone fragment H1 or H2B, for example). The transfer peptides described in this Application therefore have a general ligand structure for a membrane receptor-ligand for the outer nuclear membrane-basic peptide. Such a structure was proposed in order to improve the specificity of the complex towards target cells, but has a toxicity level of the same order as that of the liposomes; in addition, the construct should be adapted as a function of the target cells (presence of specific receptors on the target cells), and International Application WO 95/31557 which describes a transfection vector comprising a synthetic peptide and the nucleic acid to be transfected. The synthetic peptide comprises a polymeric chain of basic amino acids, preferably at the C-terminal position (10–50 amino acids, such as lysine, arginine and ornithine), an NLS peptide (6–15 amino acids, such as the NLS sequence of the SV40 T antigen, the NLS sequence of the polyoma T antigen, the NLS sequence of adenovirus E1a or the NLS sequence of adenovirus E1b, preferably at the N-terminal position and a hinge region of neutral amino acids (6–50 amino acids selected from glycine, alanine, leucine and isoleucine), between the polymeric chain and the NLS peptide. The preferred NLS sequence is the sequence of the SV40 virus T antigen (small sequence of basic amino acids: PKKKRKV SEQ ID NO: 25), which is efficient in mammalian cells or a short hydrophobic sequence which contains one or more basic amino acids (KIPIK SEQ ID NO:43). The hinge sequence comprises 6–26 neutral amino acids selected solely from Gly (G), Ala (A), Leu (L) and Ile (I). The peptide:DNA ratio (by weight) is between 1:1 and 1:10. The peptide described in this document passes across the cell membrane with difficulty and that is the reason why it is recommended, in this International Application, to treat the cells before the transfection: the cells are treated with a hypertonic solution, and then with a hypotonic solution in the presence of the nucleic acid-peptide complex. The hypertonic solution may contain PEG (0.3 M–0.6 M) and sucrose (10–25%).

These various complexes possess the property of condensing the DNA and of promoting its combination with the cell membrane; however, they are far from being as efficient as the viral vectors, in particular because of an insufficient condensation of the DNA to be transfected and/or of the difficulties encountered by the transfected DNA in coming out of the endosome without being degraded and in penetrating into the cell nucleus.

Seeking to develop novel vectors not exhibiting the disadvantages of the viral vectors, the inventors developed the vector described in International Application WO 97/18317, which describes compositions comprising an adenoviral protein complex consisting:

A. of an adenoviral protein complex, namely:
  either of 12 pentons, each comprising at least one fibre and one penton base, excluding any other constituent element of the genome of an adenovirus, which fibre(s) and penton base are derived either from the same adenovirus, or from different adenoviruses, the said pentons being linked by the penton bases and forming a dodecahedron structure, stable to proteolytic enzymes, which complex has a molecular weight of between $4.8 \times 10^6$ and $6.6 \times 10^6$;
  or of 12 penton bases, excluding any other constituent element of the genome of an adenovirus, which penton bases are derived either from the same adenovirus, or from different adenoviruses, and form a dodecahedron structure, stable to proteolytic enzymes and in that it has a molecular weight of between $3.2 \times 10^6$ and $4 \times 10^6$.

B. of a nucleic acid sequence to be transfected, and

C. of a ligand between the adenoviral protein complex and the nucleic acid, such as peptides whose N-terminal portion comprises the N-terminal amino acid sequence of a fibre of an adenovirus of any serotype (region for attachment to the adenoviral protein complex) and whose C-terminal portion comprises a polylysine or a polyarginine.

The transfection vectors described in this Application allow the internalization of the nucleic sequence to be transfected and increase the permeability of the endosomes; this is, however, a relatively complex structure which mimics the behaviour of adenoviruses; indeed, the adenoviral particles are relatively complex and comprise several substructures; in particular the outer part or capsid is formed predominantly of three proteins: the hexon, the penton base and the fibre; the fibre allows the attachment of the virion to a cell receptor, whereas the penton base allows the internalization of the virion.

Continuing their research studies, the inventors have found that, unexpectedly, a peptide derived from the adenovirus fibre protein is capable of efficiently transfecting nucleic acid sequences or proteins, in the absence of liposomes and of the treatment of cells.

SUMMARY OF THE INVENTION

The subject of the present invention is a peptide vector for transfecting a chemical substance selected from the group consisting of nucleic acid sequences, proteins, peptides and pharmacologically active chemical substances, characterized in that it contains, in addition to the said chemical substance, at least one transfecting peptide derived from the whole or part of an adenovirus fibre and comprising at least one region consisting of at least 50% of hydrophobic amino acids selected from the group consisting of alanine, valine, phenylalanine, isoleucine, leucine, proline and methionine.

In accordance with the invention, the said peptide is derived from a fibre of an adenovirus selected from the group consisting of Ad2, Ad3, Ad4, Ad7, Ad8, Ad9, Ad11, Ad12, Ad15, Ad16, Ad21, Ad40, Ad41, FAV1 (CELO) and FAV7 or from a fragment of the SV40 virus Vp3 protein.

According to an advantageous embodiment of the said transfection vector, the said transfecting peptide comprises at least:
  a segment of an NLS sequence derived from an adenovirus fibre comprising between 4 and 5 amino acids and including a sequence selected from the group consisting of the following sequences: $X_0$-Lys-Arg-Val-Arg ($X_0$KRVR) (SEQ ID NO:1), $X_0$-Lys-Arg-Ala-Arg ($X_0$KRAR) (SEQ ID NO:2), $X_0$-Lys-Arg-Ser-Arg ($X_0$KRSR) (SEQ ID NO:3), $X_0$-Lys-Arg-Leu-Arg ($X_0$KRLR) (SEQ ID NO:4), $X_0$-Lys-Arg-Thr-Arg ($X_0$KRTR) (SEQ ID NO:5), $X_0$-Pro-Lys-Lys-Pro-Arg ($X_0$PKKPR) (SEQ ID NO:6), in which $X_0$ is zero or represents Thr (T), Ala (A), Ser-Lys (SK) or Ser (S), or a segment of the SV40 virus Vp3 protein and in particular the sequence GPNKKKRKL (SEQ ID NO:24),
  a hydrophobic sequence comprising between 7 and 50 amino acids, derived from an adenovirus fibre and selected from the group consisting of at least one of the following sequences $X_1$-Phe-Asn-Pro-Val-Tyr-Pro-Tyr-$X_2$ ($X_1$FNPVYPYX$_2$) (SEQ ID NO:7), $X_1$-Phe-Asp-Pro-Val-Tyr-Pro-Tyr-$X_2$ ($X_1$FDPVYPYX$_2$) (SEQ ID NO:8), in which:

X₁ is zero or represents a sequence of at most 43 amino acids, preferably a sequence of 5 to 15 amino acids, comprising hydrophobic and/or polar and/or acidic charged amino acids, and in particular one of the following sequences: Leu-Ser-Asp-Ser (LSDS) (SEQ ID NO:9), Leu-Ser-Thr-Ser (LSTS) (SEQ ID NO:10), Leu-Ser-Ser-Ser (LSSS) (SEQ ID NO:11), Pro-Ser-Glu-Asp-Thr (PSEDT) (SEQ ID NO:12), Val-Asp-Asp-Gly (VDDG) (SEQ ID NO:13), Thr-Gln-Tyr-Ala-Glu-Glu-Thr-Glu-Glu-Asn-Asp-Asp (TQYAEETEENDD) (SEQ ID NO:14) or $X_3$-Glu-Asp-Asp ($X_3$EDD) (SEQ ID NO:15) in which $X_3$ represents Ala (A), Val (V), Leu (L), Phe (F) or Ile (I) and $X_2$ is zero or represents a sequence of at most 43 amino acids, preferably a sequence of 5 to 15 amino acids, comprising hydrophobic and/or polar and/or charged amino acids, and in particular one of the following sequences: Glu-Asp-Glu-Ser (EDES) (SEQ ID NO:16), Asp-Thr-Glu-Thr (DTET) (SEQ ID NO:17), Asp-Ala-Asp-Asn (DADN) (SEQ ID NO:18), Asp-Pro-Phe-Asp (DPFD) (SEQ ID NO:19), Gly-Tyr-Ala-Arg (GYAR) (SEQ ID NO:20), Glu-His-Tyr-Asn (EHYN) (SEQ ID NO:21), Asp-Thr-Ser-Ser (DTSS) (SEQ ID NO:22) or Asp-Thr-Phe-Ser (DTFS) (SEQ ID NO:23) and a polymeric sequence of basic amino acids or a cationic polymeric sequence or a polyalcohol.

There are understood by:

hydrophobic amino acids, the following amino acids: Ala, Val, Leu, Ile, Pro, Phe and Met;

acidic charged amino acids, the following amino acids: Asp and Glu;

basic charged amino acids, the following amino acids: Lys, Arg and ornithine; and neutral polar amino acids, the following amino acids: Gly, Ser, Thr, Cys, Tyr, Asn, Gln, His and Trp.

Advantageously, the said transfecting peptide is branched and comprises at least two fragments which are derived from an adenovirus fibre; the said fragments each comprise a segment of an NLS sequence and a hydrophobic sequence, as defined above and are linked to each other by a polymeric sequence such as a polymeric sequence of basic amino acids.

When the chemical substance is a nucleic acid sequence, it is selected from genes which encode a polypeptide having a therapeutic activity, antisense sequences and ribozymes.

In the case of a coding sequence, it comprises, in addition, an active promoter for the expression of the polypeptide.

The said promoter is in particular selected from the group consisting of constitutive promoters and inducible promoters.

Surprisingly, such a transfecting peptide vector comprising no lipids (in the form of liposomes, for example) or penton base is capable of efficiently transfecting in particular nucleic acid sequences of any size, up to the nucleus and without poisoning the transfected cell.

In all cases, the exogenous nucleic acid sequence, the protein of interest or any other chemical substance, combined with the said transfection vector penetrates into the cell (internalization).

Surprisingly, the transfecting peptide-cell receptor interaction significantly increases both the internalization of the transfection vector and the permeability of the endosomes, which significantly increases the passage of the exogenous nucleic acid, of the protein of interest or of any other chemical substance from the endosomes to the cytoplasm and to the nucleus, in comparison with the use of a vector including lipids (in the form of liposomes, for example).

Such transfecting peptide vectors prove surprisingly more efficient and less toxic than compositions containing liposomes (cationic lipids or lipofectants).

According to another advantageous embodiment of the said transfection vector, the said transfecting peptide comprises at least:

a segment of an NLS sequence derived from an adenovirus fibre comprising between 4 and 5 amino acids and including a sequence selected from the group consisting of the following sequences: $X_0$-Lys-Arg-Val-Arg ($X_0$KRVR) (SEQ ID NO:1), $X_0$-Lys-Arg-Ala-Arg ($X_0$KRAR) (SEQ ID NO:2), $X_0$-Lys-Arg-Ser-Arg ($X_0$KRSR) (SEQ ID NO:3), $X_0$-Lys-Arg-Leu-Arg ($X_0$KRLR) (SEQ ID NO:4), $X_0$-Lys-Arg-Thr-Arg ($X_0$KRTR) (SEQ ID NO:5), $X_0$-Pro-Lys-Lys-Pro-Arg ($X_0$PKKPR) (SEQ ID NO:6), in which $X_0$ is zero or represents Thr (T), Ala (A), Ser-Lys (SK) or Ser (S), or a segment of the SV40 virus Vp3 protein and in particular the sequence GPNKKKRKL (SEQ ID NO:24), a hydrophobic sequence comprising between 7 and 50 amino acids, derived from an adenovirus fibre and selected from the group consisting of at least one of the following sequences $X_1$-Phe-Asn-Pro-Val-Tyr-Pro-Tyr-$X_2$ ($X_1$FNPVYPY$X_2$) (SEQ ID NO:7), $X_1$-Phe-Asp-Pro-Val-Tyr-Pro-Tyr-$X_2$ ($X_1$FDPVYPY$X_2$) (SEQ ID NO:8), in which:

$X_1$ is zero or represents a sequence of at most 43 amino acids, preferably a sequence of 5 to 15 amino acids, comprising hydrophobic and/or polar and/or acidic charged amino acids, and in particular one of the following sequences: Leu-Ser-Asp-Ser (LSDS) (SEQ ID NO:9), Leu-Ser-Thr-Ser (LSTS) (SEQ ID NO:10), Leu-Ser-Ser-Ser (LSSS) (SEQ ID NO:11), Pro-Ser-Glu-Asp-Thr (PSEDT) (SEQ ID NO:12), Val-Asp-Asp-Gly (VDDG) (SEQ ID NO:13), Thr-Gln-Tyr-Ala-Glu-Glu-Thr-Glu-Glu-Asn-Asp-Asp (TQYAEETEENDD) (SEQ ID NO:14) or $X_3$-Glu-Asp-Asp ($X_3$EDD) (SEQ ID NO:15) in which $X_3$ represents Ala (A), Val (V), Leu (L), Phe (F) or Ile (I) and $X_2$ is zero or represents a sequence of at most 43 amino acids, preferably a sequence of 5 to 15 amino acids, comprising hydrophobic and/or polar and/or charged amino acids, and in particular one of the following sequences: Glu-Asp-Glu-Ser (EDES) (SEQ ID NO:16), Asp-Thr-Glu-Thr (DTET) (SEQ ID NO:17), Asp-Ala-Asp-Asn (DADN) (SEQ ID NO:18), Asp-Pro-Phe-Asp (DPFD) (SEQ ID NO:19), Gly-Tyr-Ala-Arg (GYAR) (SEQ ID NO:20), Glu-His-Tyr-Asn (EHYN) (SEQ ID NO:21), Asp-Thr-Ser-Ser (DTSS) (SEQ ID NO:22) or Asp-Thr-Phe-Ser (DTFS) (SEQ ID NO:23), which transfecting peptide is combined with a polymeric sequence of basic amino acids, a cationic polymer or a polyalcohol.

According to another advantageous embodiment of the said transfecting peptide vector, the polymeric sequence of basic amino acids comprises between 10 and 50 amino acid residues, selected from the group consisting of lysine, arginine and ornithine.

According to another advantageous embodiment of the said transfecting peptide vector, the cationic polymeric sequence is selected from the group consisting of polyamines and quaternary ammonium polymers; a preferred polyamine is polyethyleneimine (PEI).

In accordance with the invention, the said polyalcohol is preferably a $C_3$–$C_{20}$, and in particular glycerol or dextrans.

According to another advantageous embodiment of the said transfecting peptide vector, the NLS sequence is at the N-terminal end of the transfecting peptide and the polymeric sequence of basic amino acids is at the C-terminal end of the said transfecting peptide.

According to another advantageous embodiment of the said transfecting peptide vector, when the chemical substance is a nucleic acid, the transfecting peptide/nucleic acid ratio is between 0.3:1 and 15:1, preferably between 2:1 and 6:1, preferably between 4:1 and 6:1.

According to another advantageous embodiment of the said transfecting peptide vector, it is combined with a targeting ligand.

The subject of the invention is also a composition, characterized in that it essentially consists of a transfer vector as defined above and a suitable vehicle selected from the group consisting of bile salts, antiproteases, cyclodextrins and derivatives thereof, antiseptics and polyols.

The compositions according to the invention have many applications as medicaments, in human and veterinary medicine:

in human and-animal gene therapy, in particular in hereditary diseases, as antiviral agents (antisense sequences or ribozymes), as immunogenic or vaccinal agents, as antibacterial or anticancer agents, and the like.

The subject of the present invention is also a method of transfecting eukaryotic cells in vitro with a chemical substance selected from the group consisting of nucleic acid sequences, proteins, peptides and pharmacologically active chemical substances, characterized in that it comprises the bringing into contact and the incubation of a transfecting peptide vector in accordance with the invention, in a dilution buffer comprising 100–150 mM NaCl with eukaryotic cells for 15 to 120 minutes at room temperature, the chemical substance to be transfected:transfecting peptide ratio being between 0.3:1 and 15:1, preferably between 2:1 and 6:1, preferably between 4:1 and 6:1.

BRIEF DESCRIPTION OF THE DRAWINGS

In addition to the preceding features, the invention also comprises other features which will emerge from the description which follows, which refers to exemplary embodiments of the method which is the subject of the present invention as well as to the accompanying drawings, in which:

FIG. 7 represents a few sequences (SEQ ID NO: 26–42) of adenovirus fibres.

DETAILED DESCRIPTION AND EXAMPLES

Figure 1:
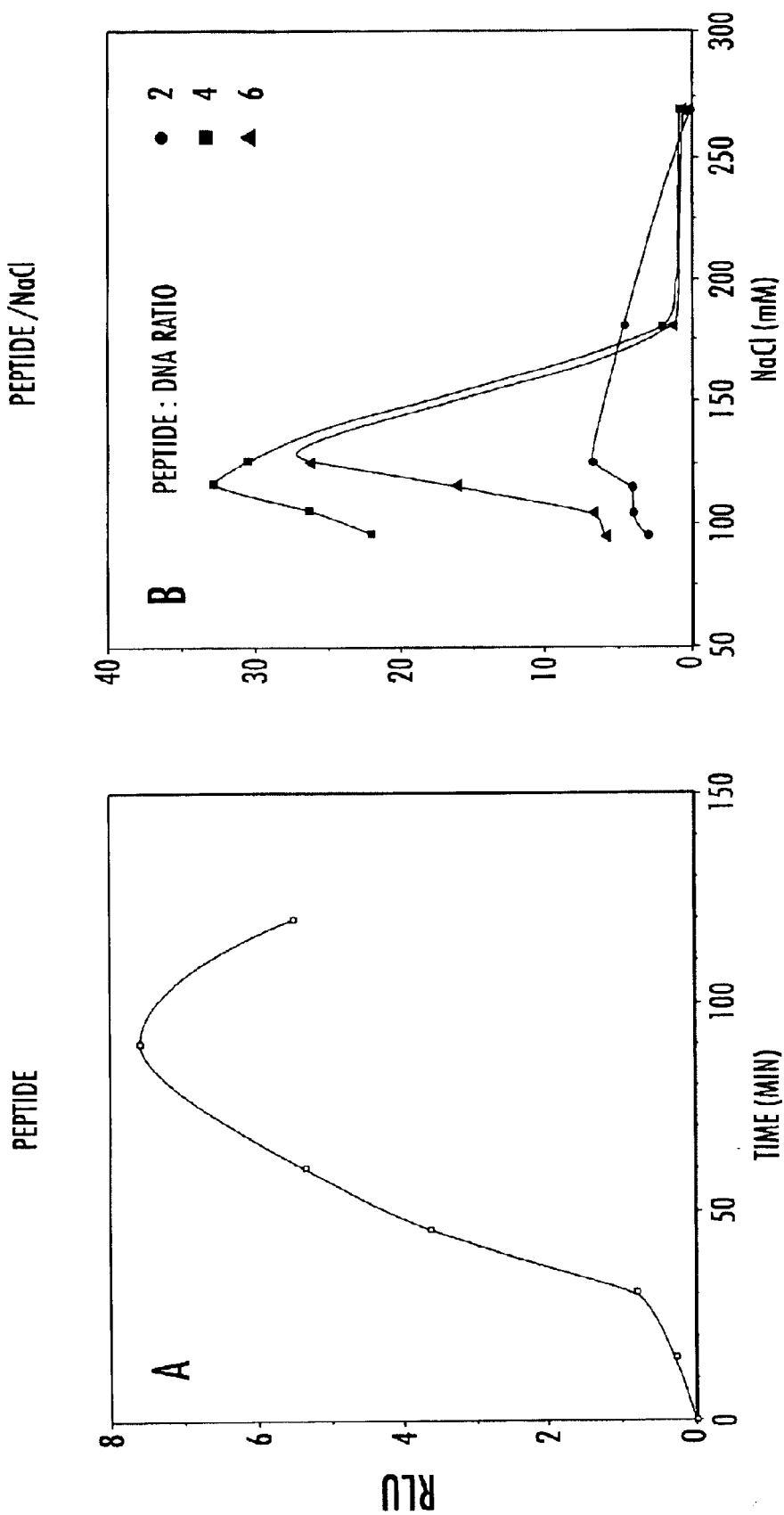
FIG. 1 illustrates the transfer of the luciferase gene with peptide I, as a function of time (FIG. 1A) or as a function of the NaCl concentration (FIG. 1B)

It should be clearly understood, however, that these examples are given solely by way of illustration of the subject of the invention and do not constitute in any manner a limitation thereof.

EXAMPLE 1

Materials and Methods

Cells, Plasmid and Peptides:

The HeLa cells are cultured at 37° C. in an EMEM medium supplemented with 10% foetal calf serum under an atmosphere containing 5% $CO_2$.

A luciferase reporter vector (plasmid pGL3, Promega) is used to demonstrate the transfection.

The peptide IC comprises sequence No. 2, sequence No. 10, sequence No. 7, sequence No. 16, from the N-terminal end to the C-terminal end and 10 lysines; this peptide corresponds to the 20 N-terminal residues of the Ad3 fibre. Peptide I contains these same 20 N-terminal amino acids of the Ad3 fibre and 20 lysines; the peptides were obtained by solid-phase synthesis, followed by HPLC purification.

This peptide I is labelled with fluorescein; peptides comprising 10 lysines instead of 20 were also prepared. The integrity of all the peptides is verified by mass spectroscopy.

Retardation Gel:

500 ng of plasmid DNA (pGL3) are preincubated with various quantities of peptides for 5 min at room temperature, and then subjected to electrophoresis on a 1% agarose gel prepared in a TBE buffer.

After electrophoresis at 50 V in the TBE buffer for 30 min, the DNA on the gel being stained with ethidium bromide and visualized under ultraviolet light.

Transfections:

1.5 to 12 μg of peptide I in 50 μl of dilution buffer (20 mM Tris, pH 7.4, 150 mM NaCl) are incubated with 1.5 μg of plasmid pGL3 in 250 μl of EMEM medium for 15 to 30 min at room temperature.

The mixture of DOTAP or of DOSPER with 1.5 μg of plasmid pGL3 is prepared according to the manufacturer's instructions (Boehringer). For the studies of the effect of the peptide on transfection in the presence of liposomes, portions of peptides are mixed with DOTAP or DOSPER in the dilution buffer defined above for 15 to 30 min at room temperature, and then 1.5 μg of plasmid pGL3 are added and incubated for 15 min at room temperature.

The transfections are carried out in plates comprising 24 wells (Beckton Dickinson) with 1.5×$10^5$ cells/well (confluence of about 50%) for 1 h at 37° C. After 24 h, the light emission is measured in the cell lysates with the Promega Luciferase Assay System test.

Haemolytic Test:

Human erythrocytes are washed 3 times with PBS buffer. $10^6$ erythrocytes are incubated with 6 μg of peptide I for various periods of time at 37° C. After centrifugation at 10,000 g for 5 min, the optical density of the supernatant is measured at 540 nm.

Internalization of the Peptide:

HeLa cells, cultured on cover slips ($10^5$ cells/cover slip) are treated with 3% bovine serum albumin in EMEM for 15 min at 37° C.

The cells are washed twice with PBS buffer, incubated with 40 µg/ml of peptide I labelled with fluorescein for various durations at 37° C., fixed with 2% paraformaldehyde in PBS for 20 min at 37° C., washed with PBS and stained with 1 µg/ml of propidium iodide in PBS for 5 min at room temperature.

The cover slips are mounted on a microscope slide with 1,4-diazabicyclooctane (Sigma) and observed under an MRC600 confocal microscope (BioRad).

Results

Cell Transfection With Peptide I:

All the experiments were carried out with HeLa cells transfected with the plasmid pGL3 (Stratagene) carrying the luciferase gene. For peptide I/DNA ratios equal to 2, the optimum time for interaction between the transfecting complexes and the cells is between 60 and 120 min (FIG. 1A).

The effect of the NaCl concentrations was tested for 1 h of transfection on gene expression measured 24 h after transfection (FIG. 1B).

A transfection optimum exists for peptide I/DNA ratios of between 4 and 6 and for an NaCl concentration of 125 mM. Concentrations of less than 100 mM and greater than 150 mM appear to be inhibitory.

Figure 2:
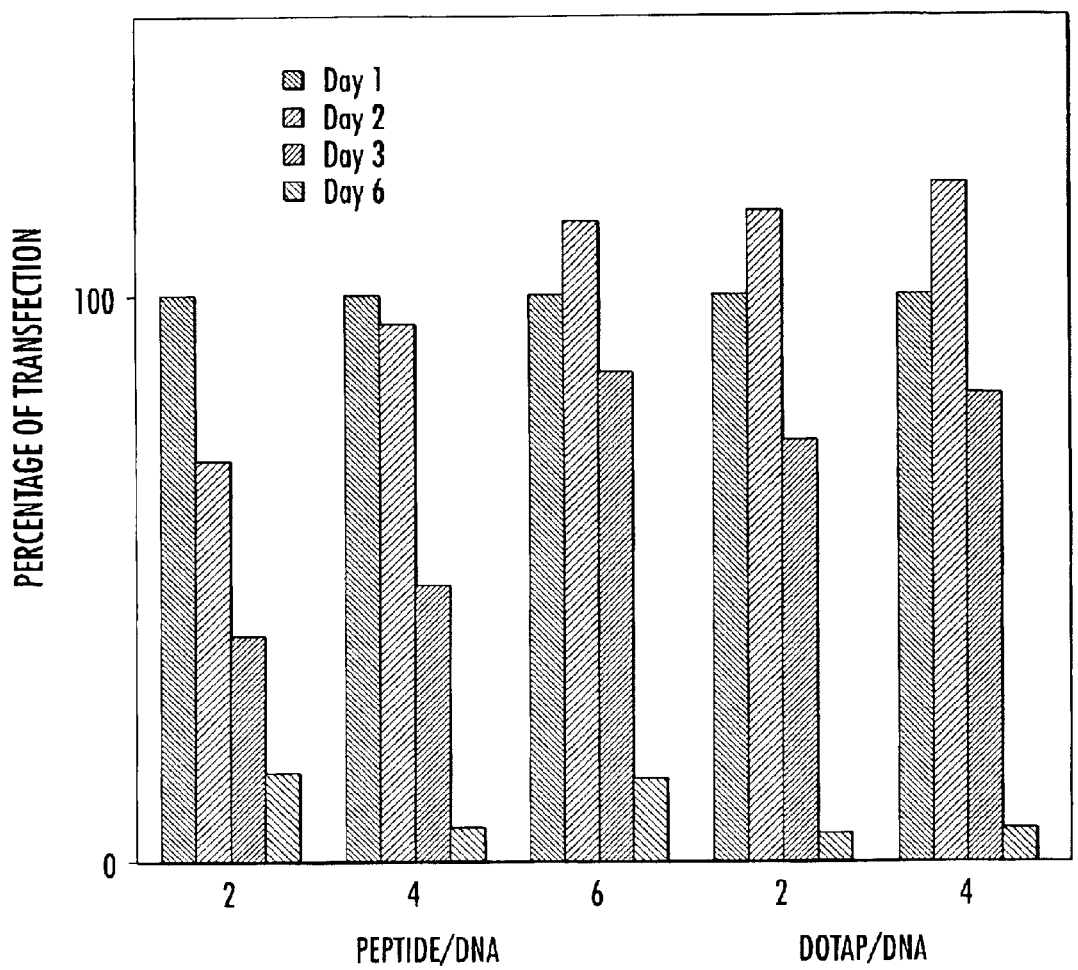
FIG. 2 illustrates the kinetics of the expression of the luciferase gene; this figure comprises on the x-axis the transfecting peptide/DNA or DOTAP/DNA ratios and on the y-axis the percentage of transfection at D1 (v), D2 (□), D3 (□) and D6 (□)

The expression of the transgene may be observed up to 6 days after transfection (FIG. 2). However, the addition of 2% serum completely abolishes the transfection with peptide I.

The behaviour of the DNA/peptide complexes is analysed on retardation gels. In theory, 526 peptide molecules are necessary to neutralize the phosphate charges carried by the plasmid (5256 bp), which means that 322 ng of peptide I are necessary for complete neutralization of 500 ng of plasmid.

Figure 3:
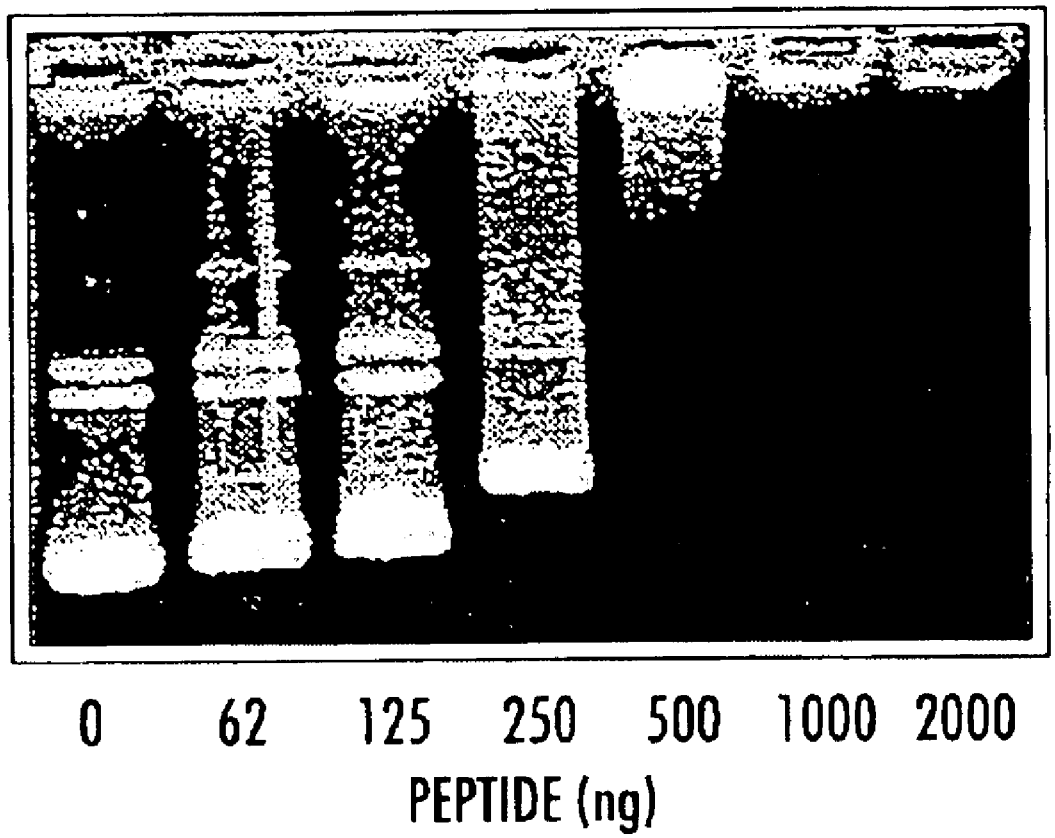
FIG. 3 represents the migrations obtained on a retardation gel, as a function of the quantity of transfecting peptide.

FIG. 3 shows that incubation with 250 ng of peptide causes retardation in the migration of the DNA and the addition of 500 ng of peptide completely stops its migration, which is in agreement with the theoretical considerations set out above.

The highest transfection efficiency is observed when an excess of neutralizing peptide charges relative to the DNA of the order of 4 exists (FIG. 1B), which confirms that the transfer of the gene occurs only in the presence of an excess of positive charges.

Parameters Involved in the Efficiency of Transfection With the Peptide According to the Invention:

The peptides according to the invention comprise essentially 3 domains: the nuclear localization signal, the hydrophobic domain and the basic polymer.

To study the effect of the structure of the peptide on the transfection of DNA, a series of peptides [lacuna], in which the various portions of peptide I have been removed, whose sequences are illustrated in Table I below:

TABLE I

| Peptide | Sequences * |
|---|---|
| I | A K R A R L S T S F N P V Y P Y E D E S - $K_{20}$ = <br> SEQ ID NO: 2 + SEQ ID NO: 10 + SEQ ID NO: 7 + SEQ ID NO: 16-$K_{20}$ (SEQ ID NO: 44) |
| IC | A K R A R L S T S F N P V Y P Y E D E S - $K_{10}$ = <br> SEQ ID NO: 2 + SEQ ID NO: 10 + SEQ ID NO: 7 + SEQ ID NO: 16-$K_{10}$ (SEQ ID NO: 45) |
| IE | A K R A R L S T S E D E S-$K_{10}$ = <br> SEQ ID NO: 2 + SEQ ID NO: 10 + SEQ ID NO: 16-$K_{10}$ (SEQ ID NO: 46) |
| ID | L S T S F N P V Y P Y E D E S-$K_{20}$ = <br> SEQ ID NO: 10 + SEQ ID NO: 7 + SEQ ID NO: 16-$K_{20}$ (SEQ ID NO: 47) |

TABLE I-continued

| Peptide | Sequences * |
|---|---|
| IA | A K R A R L S T S F N P V Y P Y E D E S = <br> SEQ ID NO: 2 + SEQ ID NO: 10 + SEQ ID NO: 7 + SEQ ID NO: 16 (SEQ ID NO: 48) |
| LII | A K R A R L S T S F N P V Y P Y E D E S <br> $\diagdown$ <br> $K_{19}$ <br> $\diagup$ <br> A K R A R L S T S F N P V Y P Y E D E S <br> (SEQ ID NO: 49) <br> (for each branch: SEQ ID NO: 2 + SEQ ID NO: 10 + SEQ ID NO: 7 + SEQ ID NO: 16) |

* in which $X_0$ = A.

The results obtained with these various peptides are illustrated in Table II below.

TABLE II

| Peptide (µg) | DNA (µg) | RLU/10 s/$10^5$ cells × $10^3$ |
|---|---|---|
| Peptide I | | |
| 3 | 1.5 | 450 |
| 6 | 1.5 | 4920 |
| 9 | 1.5 | 1450 |
| 12 | 1.5 | 1170 |
| Peptide IC | | |
| 3.6 | 1.5 | 1 |
| 9 | 1.5 | 2870 |
| 12 | 1.5 | 1330 |
| Peptide IE | | |
| 3 | 1.5 | 1 |
| 6 | 1.5 | 10 |
| 9 | 1.5 | 110 |
| 12 | 1.5 | 330 |
| Peptide ID | | |
| 3–12 | 1.5 | 1 |
| Peptide IA | | |
| 3–12 | 1.5 | 1 |
| Peptide $K_{10}$ | | |
| 3–12 | 1.5 | 1 |
| Peptide $K_{20}$ | | |
| 3–12 | 1.5 | 1–10 |

The results presented in Table II show that the transfection efficiency depends on the presence of the nuclear localization signal sequence of the adenovirus fibre protein.

There is no transfection when the NLS domain (peptide ID), polylysine (peptide IA) or both the NLS domain and the hydrophobic region (peptide $K_{10}$ and peptide $K_{20}$) are removed. The removal of the hydrophobic domain between the NLS portion and the polylysine portion induces a significant effect: this peptide (peptide IE) is approximately 30 times less efficient than peptide IC. Even if peptide ID is still capable of attaching and condensing the DNA and of entering into the cell, it appears nevertheless incapable of transporting this DNA into the nucleus.

It is also evident from these results that when the number of lysines present in the polylysine polymer (peptide IC) is reduced, a modest negative effect is observed on the transfection efficiency which can be compensated for by increasing the quantity of peptide necessary for an efficient transfer.

Table III below illustrates other results obtained with peptide I or peptide IA, in the presence of glycerol or of PEI and peptide LII.

TABLE III

| Peptide (or PEI) (μg) | DNA (μg) | RLU/10 s/$10^5$ cells × $10^3$ |
|---|---|---|
| Peptide I | | |
| 6 | 1.5 | 12,600 |
| 6 (+ 10% glycerol) | 1.5 | 34,900 |
| 6 (+ 0.1% DMSO) | 1.5 | 11,320 |
| Peptide LII | | |
| 1.5 | 1.5 | 0 |
| 3 | 1.5 | 5200 |
| 6 | 1.5 | 2400 |
| PEI | | |
| 3 | 1.5 | 66,400 |
| 4 | 1.5 | 51,200 |
| Peptide IA + PEI | | |
| 1.2 μg | 1.5 | 104,000 |
| 1.6 μg | 1.5 | 84,800 |

The peptide vector comprising peptide I and PEI (covalent complex) is more efficient than PEI (polyethyleneimine) alone.

The transfection efficiency is significantly greater in the case of the covalent complex.

It can be said that 1 μg of peptide I/PEI gives 54,000–67,000 RLU, while 1 μg of PEI gives 13,000–22,000 RLU.

Effect of the Peptide on Transfection in the Presence of Liposomes:

Two liposomes were used, the liposome DOTAP and the liposome DOSPER, both marketed by Boehringer.

They consist of cationic lipids with internal ester bonds capable of being degraded by cellular lipases or esterases, which ought to confer on these liposomes a cytotoxicity lower than that observed with other liposomes.

Figure 4:
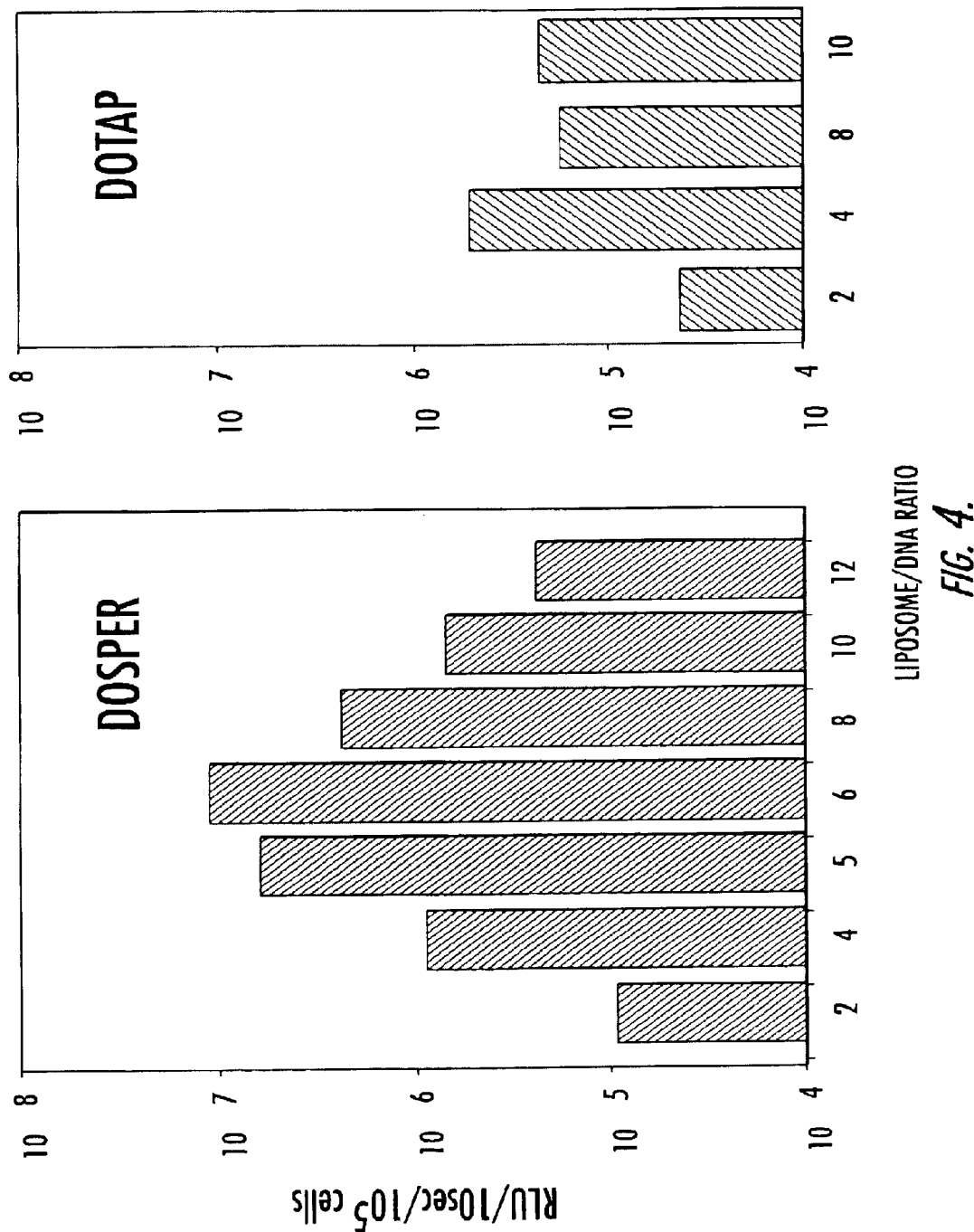
FIG. 4 illustrates the transfections obtained with the liposomes DOSPER and DOTAP; this figure comprises on the x-axis the liposome/DNA ratios and on the y-axis the RLU (Relative Light Unit)/10 sec/$10^5$ cells.

The conditions for transfecting the HeLa cells were optimized for the liposomes alone (FIG. 4). The transfection with the liposome DOTAP leads to lower efficiencies than those observed with the liposome DOSPER; however, the transfections with the liposome DOTAP tend to show a plateau above a certain DNA/liposome ratio, whereas the transfections with the liposome DOSPER show a peak. For the simultaneous peptide/liposome transfections, the order in which these compounds are added is important, since a higher efficiency (increase of several factors) is observed when the liposome is first mixed with the peptide (and not with the DNA) and then when the plasmid DNA is added after 15 min of incubation at room temperature.

Table IV below illustrates the results obtained.

TABLE IV

| | RLU/10 sec/$10^5$ cells × $10^3$ | | |
|---|---|---|---|
| | | Peptide I:DNA | |
| DOTAP:DNA no peptide I | | 2 | 4 |
| 2 | 9320 ± 820 | 28,900 ± 890 | 30,440 ± 2360 |
| 4 | 18,590 ± 570 | 15,050 ± 340 | 17,750 ± 750 |
| 6 | 4140 ± 640 | 3800 ± 770 | 7300 ± 150 |
| DOSPER:DNA no peptide I | 1 | 2 | 4 |
| 4 | 822 ± 78 | 3160 ± 760 | 11,102 ± 2370 | 5140 |
| 5.5 | 6880 | 18,820 | 13,760 | 12,840 |
| No liposome | | 13,550 ± 2930 | 35,500 ± 4800 |

The results illustrated in this Table IV were obtained under the following conditions:

portions of the peptide I are mixed with 1.5 μg of plasmid pGL3 in 300 μl of dilution buffer for 15 min at room temperature.

The liposome DOTAP is mixed with 1.5 μg of plasmid pGL3 in a DOTAP/DNA ratio of 2 or 4 (v/w), in 300 μl of dilution buffer for 15 min at room temperature.

Surprisingly, these results show that in the absence of liposomes, the results observed with the peptide alone in peptide/DNA ratios of 4 are superior to those observed with the liposome/peptide mixture.

Figure 5:
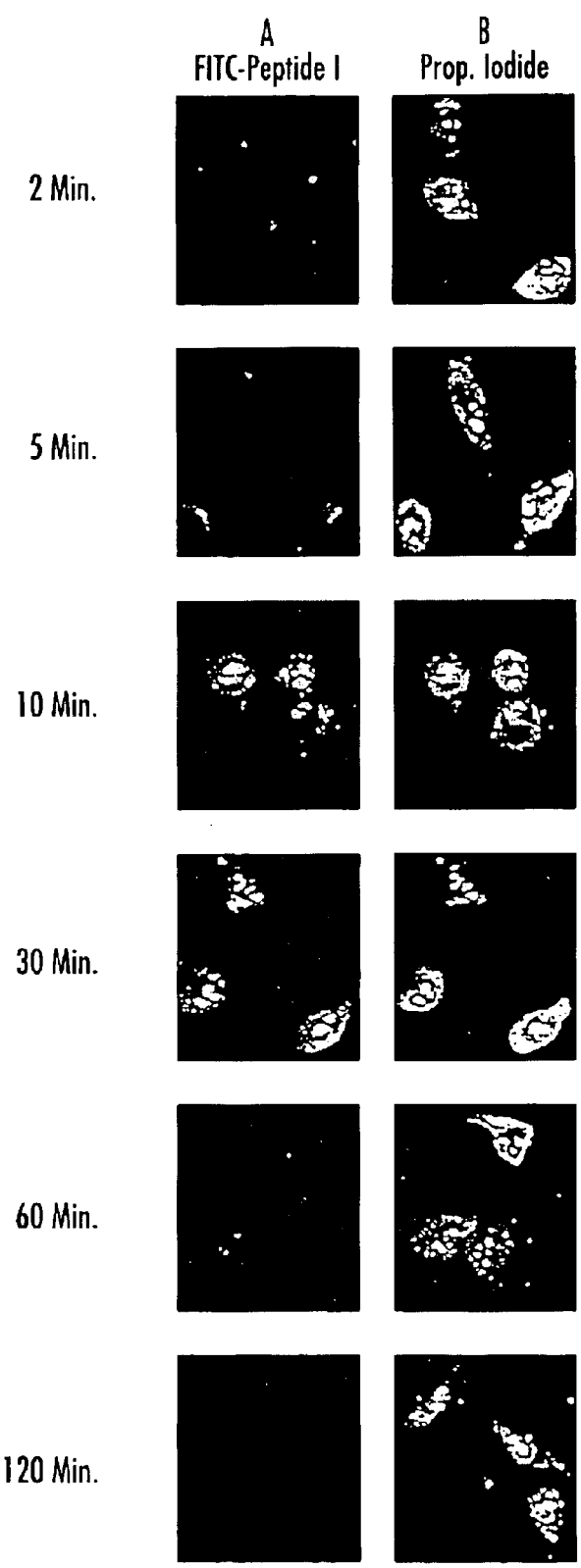
FIG. 5 illustrates the kinetics of entry into the cells of a peptide (peptide I) observed in confocal microscopy; column A shows the fluorescent peptide and column B shows the cellular nucleic acids stained with propidium iodide.

Intracellular Location of the Peptide:

The cellular distribution of the fluorescent peptide I is monitored by confocal microscopy (FIG. 5).

The first observations, carried out 2 min after the transfection, show a certain quantity of signal at the periphery of the cell.

5 to 10 min after the addition of the peptide, a strong cytoplasmic signal is observed, indicating the entry of the peptide into the cell.

At 30 min, the signal is also observed in the nucleus and a very bright signal is observed in the nucleoli. This substantial transfer into the nucleoli is particularly surprising.

The observations made between 60 and 120 min show the passage of the peptide again into the cytoplasm and at the periphery of the cell until the signal is completely lost.

The results illustrated in this FIG. 4 were obtained with peptide concentrations twice as high (40 μg/ml) as those used for the DNA transfection assays. When the usual concentrations for the transfections are used, the accumulation of peptides is slower, but follows the same steps as those specified above.

Mechanism of the Internalization of the Peptide:

A haemolytic test carried out with peptide I on erythrocytes gives negative results which show that the interaction of the cell with peptide I is not linked to the formation of pores. Since no expression of luciferase is observed when the transfections are carried out at 4° C., it appears that the mechanism of internalization of the peptide depends on endocytosis and involves the cytoskeleton.

To determine if sites for specific attachment of peptide I to the plasma membrane exist, cells were preincubated with peptide I at 4° C. for 2 h, so as to try to saturate the possible sites of attachment of the peptide.

Figure 6:
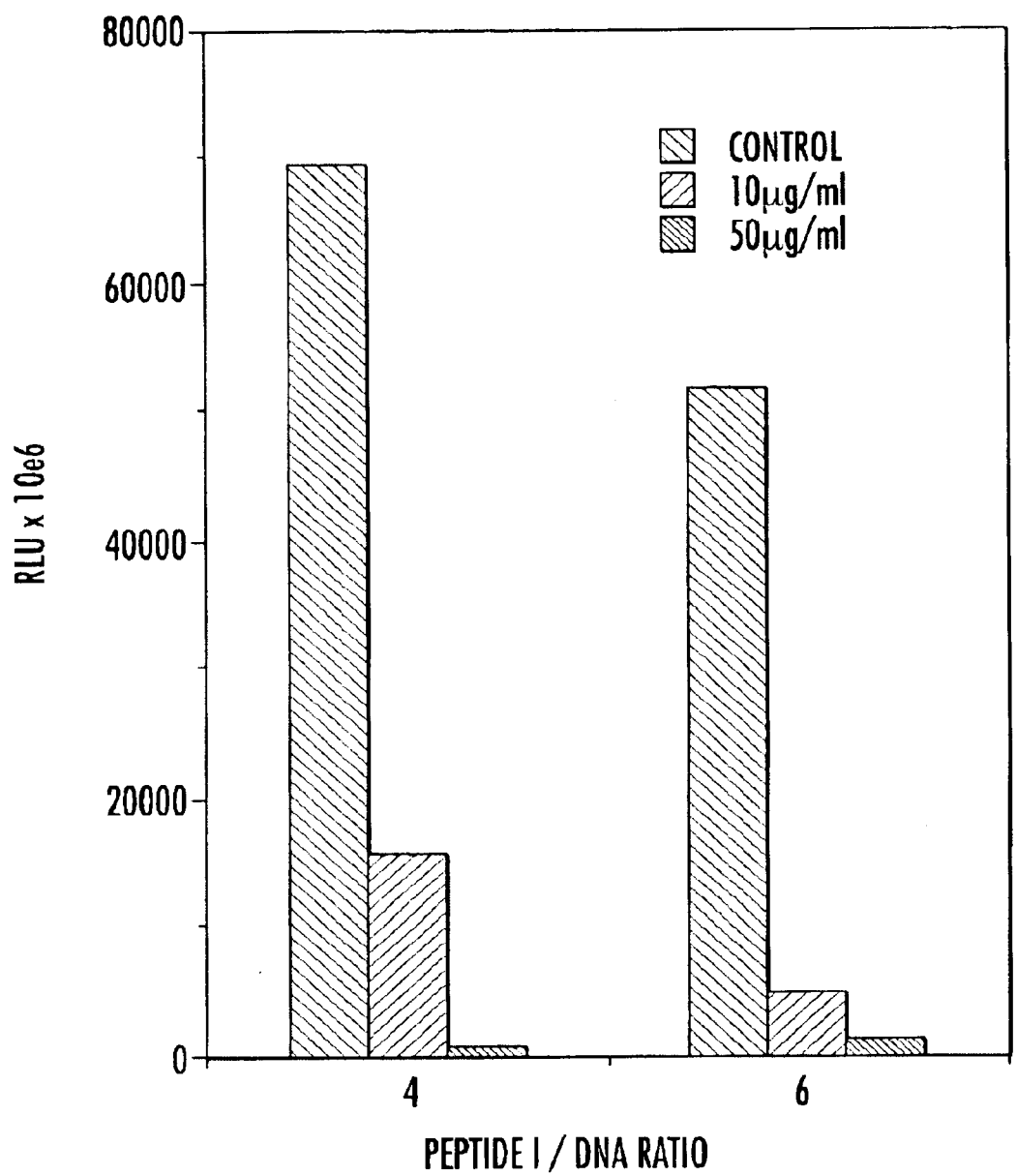
FIG. 6 illustrates the inhibition of transfection with peptide I, after preincubation with an excess of peptide I. The HeLa cells in plates comprising 24 wells are preincubated with peptide I for one hour at 4° C. at concentrations of 10 to 50 μg/ml, respectively.

This resulted in complete inhibition of transfection (FIG. 6), which indicates that the latter involves a receptor-dependent endocytosis.

Size of the Transfecting Complex:

Light scattering can be used to measure the size of the complexes and their distribution, if a mixed population is formed. Under these conditions, it is possible to study the effect of the incubation time on the formation of the transfecting complexes.

The size is measured immediately after the mixing and 1 h later. The complexes prepared by mixing the liposome DOTAP with a DNA plasmid have a diameter of about 115 nm and their size does not change during the incubation.

The DNA/peptide I complexes are larger and have a diameter of about 350–360 nm. Furthermore, the formation of the complex is a dynamic process since a rapid increase in size is observed as a function of the incubation time when more than 90% of the complexes reach a diameter of 660–1100 nm after 1 h.

The size and the distribution of the complexes with peptide I is similar regardless of the peptide/DNA ratio (from 1 to 8).

The effect of the size of the complex on the transfection efficiency was studied using complexes prepared by varying the period of incubation at room temperature. The results are illustrated in Table V below.

TABLE V

RLU/10 sec/$10^5$ cells × $10^3$

| | Preincubation time at room temperature (min) | | | | |
|---|---|---|---|---|---|
| Peptide:DNA | 0 | 15 | 30 | 60 | 120 |
| Experiment 1: | | | | | |
| 2 | | 410 | | 150 | 827 |
| 4 | | 2540 | | 1900 | 1460 |
| 6 | | 702 | | 3460 | 980 |
| Experiment 2: | | | | | |
| 4 | 400 | 3240 | 4950 | 4120 | |
| Experiment 3: | | | | | |
| 4 | 1710 | 14,550 | 23,170 | 32,175 | 6800 |

Surprisingly, with the complexes according to the invention, even very large aggregates can be transfected.

To measure the size of the transfected substance, light scattering measurements were carried out with an ion-argon laser (Spectra Physics 1161) at 488 nm and 150 mW (geometry of scattering at 90°). The spectrum is accumulated for 200 s using a Malvern 7032 correlator (Malvern Instruments) and then repeated 1 h later. All the spectra are in homodyne mode: the amplitudes of the intensity correlation function with a zero retardation are consistent with the special coherence factor β obtained with a suspension of dilute latex, namely β=0.90.

The hydrodynamic rays $R_H$ are calculated using the Malvern multimodal procedure (Pike-Ostrowsky), in order to characterize the principal rates of degradation of the field correlation function with the Stokes-Einstein equation $R_H=k_8TQ^2/(6\pi\eta\Gamma 1)$, in which Γ1 is the principal degradation rate, T is the absolute temperature of the thermal bath (298 K), Q the transfer wave vector and η the viscosity of the solvent.

As is evident from the above, the invention is not at all limited to its embodiments, methods of implementation and methods of application which have just been described more explicitly; it embraces, on the contrary, all the variants which may occur to a specialist in this field, without departing from the framework or scope of the present invention.

What is claimed is:

1. A composition for transfecting a chemical substance selected from the group consisting of nucleic acid sequences, proteins, peptides and pharmacologically active chemical substances, characterized in that it consists essentially, in addition to the said chemical substance, of one or more transfecting peptide derived from the whole or part of a fibre of an adenovirus selected from the group consisting of Ad2, Ad3, Ad4, Ad7, Ad8, Ad9, Ad11, Ad12, Ad15, Ad16, Ad21, Ad40, Ad41, FAV1 (CELO) and FAV7, which transfecting peptide comprises at least:

a segment of an NLS sequence derived from an adenovirus fibre, presenting the sequence Ala-Lys-Arg-Ala-Arg (AKRAR) (SEQ ID NO:2), a hydrophobic sequence derived from an adenovirus fibre, presenting the sequence $X_1$-Phe-Asn-Pro-Val-Tyr-Pro-Tyr-$X_2$ ($X_1$FNPVYPY$X_2$) (SEQ ID NO:7), in which:
$X_1$ is the sequence Leu-Ser-Thr-Ser (LSTS) (SEQ ID NO:10), and
$X_2$ is the sequence Glu-Asp-Glu-Ser (EDES) (SEQ ID NO:16), and a polymeric sequence of basic amino acids.

2. A composition for transfecting a chemical substance selected from the group consisting of nucleic acid sequences, proteins, peptides and pharmacologically active chemical substances, characterized in that it consists, in addition to the said chemical substance, of one or more transfecting peptide derived from the whole or part of a fibre of an adenovirus selected from the group consisting of Ad2, Ad3, Ad4, Ad7, Ad8, Ad9, Ad11, Ad12, Ad15, Ad16, Ad21, Ad40, Ad41, FAV1 (CELO) and FAV7, which transfecting peptide comprises at least:

a segment of an NLS sequence derived from an adenovirus fibre, presenting the sequence: Ala-Lys-Arg-Ala-Arg (AKRAR) (SEQ ID NO:2), a hydrophobic sequence derived from an adenovirus fibre, presenting the sequence $X_1$-Phe-Asn-Pro-Val-Tyr-Pro-Tyr-$X_2$ ($X_1$FNPVYPY$X_2$) (SEQ ID NO:7), in which:
$X_1$ is the sequence Leu-Ser-Thr-Ser (LSTS) (SEQ ID NO:10), and
$X_2$ is the sequence Glu-Asp-Glu-Ser (EDES) (SEQ ID NO:16), which transfecting peptide is combined with a polymeric sequence of basic amino acids.

3. The composition according to claim 1 or claim 2, wherein the polymeric sequence of basic amino acids comprises between 10 and 50 amino acid residues, selected from the group consisting of lysine, arginine and ornithine.

4. The composition according to claim 1 or 2, wherein the NLS sequence is at the N-terminal end of the transfecting peptide and the polymeric sequence of basic amino acids is at the C-terminal end of the said transfecting peptide.

5. The composition according to claims 1 or 2, wherein, when the chemical substance is a nucleic acid, the transfecting peptide/nucleic acid ratio is between 0.3:1 and 15:1.

6. The composition according to claims 1 or 2, combined with a targeting ligand.

7. A composition consisting, in addition to the said chemical substance and to the said transfection peptide(s) according to claim 1 or 2, of a suitable vehicle selected from the group consisting of bile salts, antiproteases, cyclodextrins and derivatives thereof, antiseptics and polyols.

8. A method of transfecting eukaryotic cells in vitro with a chemical substance selected from the group consisting of nucleic acid sequences, proteins, peptides and pharmacologically active chemical substances, characterized in that it comprises the bringing into contact and the incubation of a composition according to claim 1 or 2 in a dilution buffer comprising 100–150 mM NaCl with eukaryotic cells for 15 to 120 minutes at room temperature, the chemical substance to be transfected:transfecting peptide ratio being between 0.3:1 and 15:1.

9. A composition for transfecting a chemical substance selected from the group consisting of nucleic acid sequences, proteins, peptides and pharmacologically active chemical substances, consisting, in addition to the said chemical substance, of one or more transfecting peptide which comprises:

a segment of an NLS sequence consisting of sequence ID NO:2, a segment of a sequence consisting of sequence ID NO:10, a segment of a sequence consisting of sequence ID NO:16, and a polylysine.

10. A composition according to claim 3, wherein the polymeric sequence of basic amino acids comprises 20 lysines.

11. A composition according to claim 3, wherein the polymeric sequence of basic amino acids comprises 10 lysines.

12. A composition according to claim 5 wherein the transfecting peptide/nucleic acid ratio is between 2:1 and 6:1.

13. A method according to claim 8 wherein the ratio of substance to be transfected:transfecting peptide is between 2:1 and 6:1.

14. A method according to claim 8 wherein the ratio of substance to be transfected:transfecting peptide is between 4:1 and 6:1.

* * * * *